United States Patent [19]
Yoon

[11] Patent Number: 5,542,949
[45] Date of Patent: Aug. 6, 1996

[54] MULTIFUNCTIONAL CLIP APPLIER INSTRUMENT

[76] Inventor: InBae Yoon, 2101 Highland Ridge Dr., Phoenix, Md. 21131

[21] Appl. No.: 121,589

[22] Filed: Sep. 16, 1993

Related U.S. Application Data

[63] Continuation-in-part of Ser. No. 45,769, Apr. 14, 1993, abandoned, and Ser. No. 951,275, Sep. 28, 1992, Pat. No. 5,445,167, which is a division of Ser. No. 719,281, Sep. 18, 1991, Pat. No. 5,366,459, which is a continuation-in-part of Ser. No. 515,641, Apr. 2, 1990, Pat. No. 5,171,250, which is a continuation of Ser. No. 49,526, May 14, 1987, abandoned, said Ser. No. 45,769, Apr. 14, 1993, abandoned, is a continuation-in-part of Ser. No. 719,281, Sep. 18, 1991, Pat. No. 5,366,459, which is a division of Ser. No. 450,301, Dec. 15, 1989, Pat. No. 5,100,418, which is a continuation-in-part of Ser. No. 49,504, May 14, 1987, abandoned.

[51] Int. Cl.$^6$ ..................... A61B 17/04
[52] U.S. Cl. .................. 606/143; 606/142; 227/901
[58] Field of Search .................. 606/142, 143; 227/175–180, 901

[56] References Cited

U.S. PATENT DOCUMENTS

| | | | |
|---|---|---|---|
| 4,624,254 | 11/1986 | McGarry et al. | 606/143 |
| 4,662,373 | 5/1987 | Montgomery et al. | 606/143 |
| 5,084,057 | 1/1992 | Green et al. | 606/143 |
| 5,104,394 | 4/1992 | Knoefler | 606/143 |
| 5,156,609 | 10/1992 | Nakao et al. | 606/143 |

*Primary Examiner*—Gary Jackson
*Attorney, Agent, or Firm*—Law Offices Epstein, Edell & Retzer

[57] ABSTRACT

A multifunctional clip applier instrument includes an elongate instrument body having a proximal end received in a control housing, a distal end having one or two pairs of opposed forceps jaws spring biased apart, a plurality of surgical clips disposed in one or two clip magazines inserted into a clip cartridge removably received into the instrument body and a handle cooperating with the control housing to operate the forceps jaws to apply clips to tissue, to grasp and manipulate tissue when no clip is in the jaws, to selectively or automatically advance clips into the jaws and to selectively or automatically cut tissue after clipping.

35 Claims, 12 Drawing Sheets

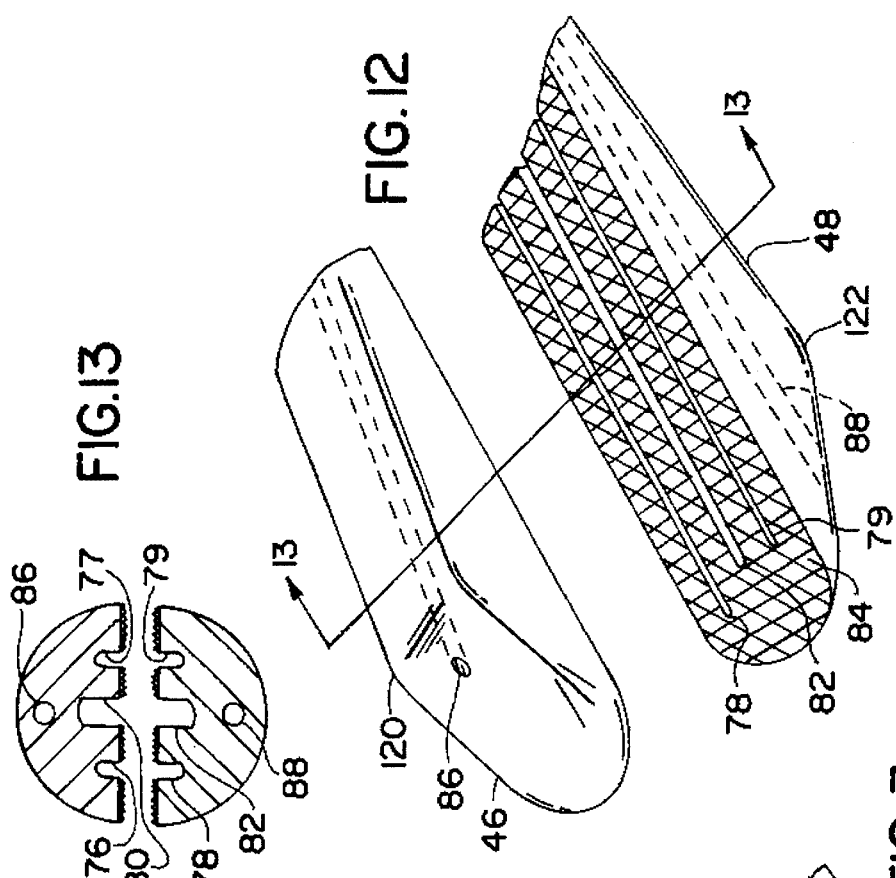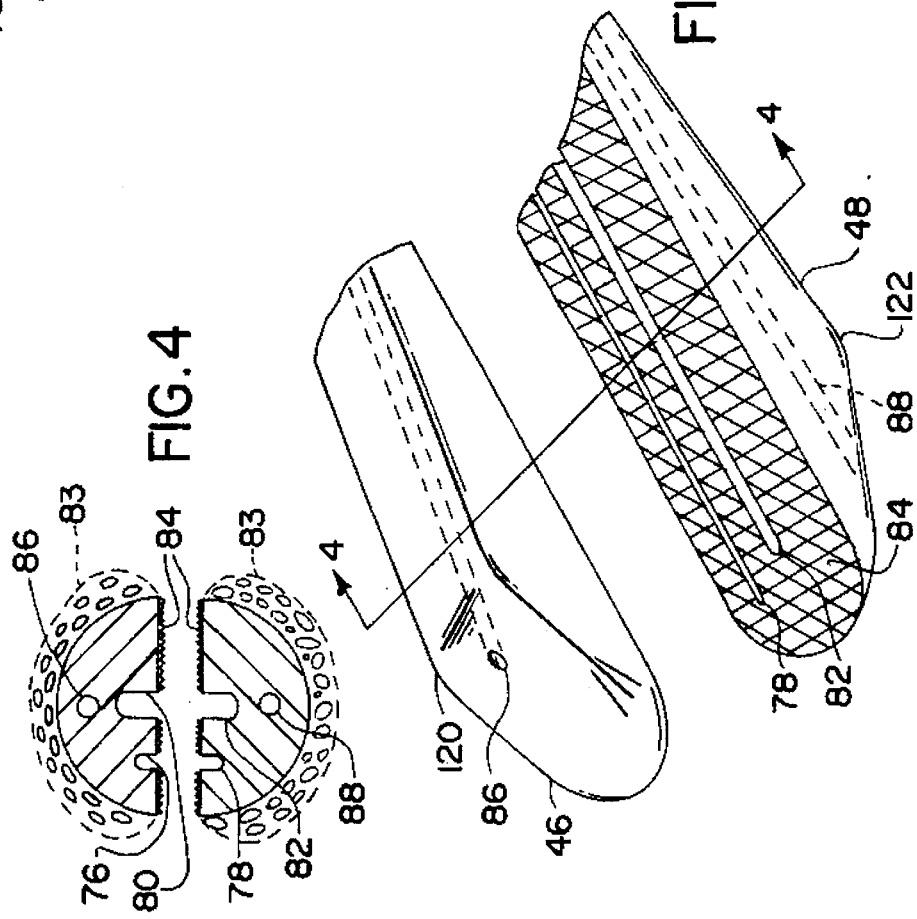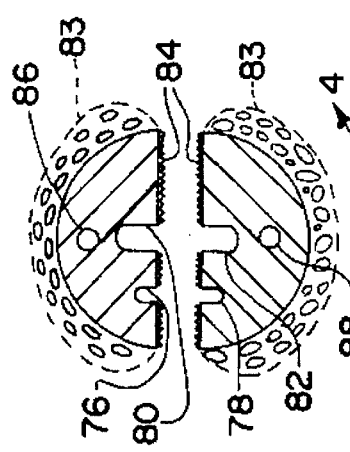

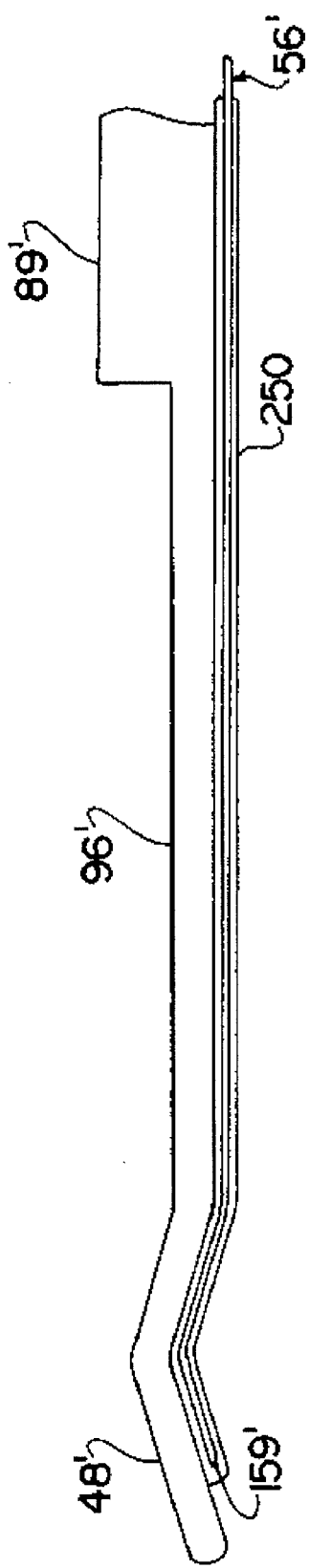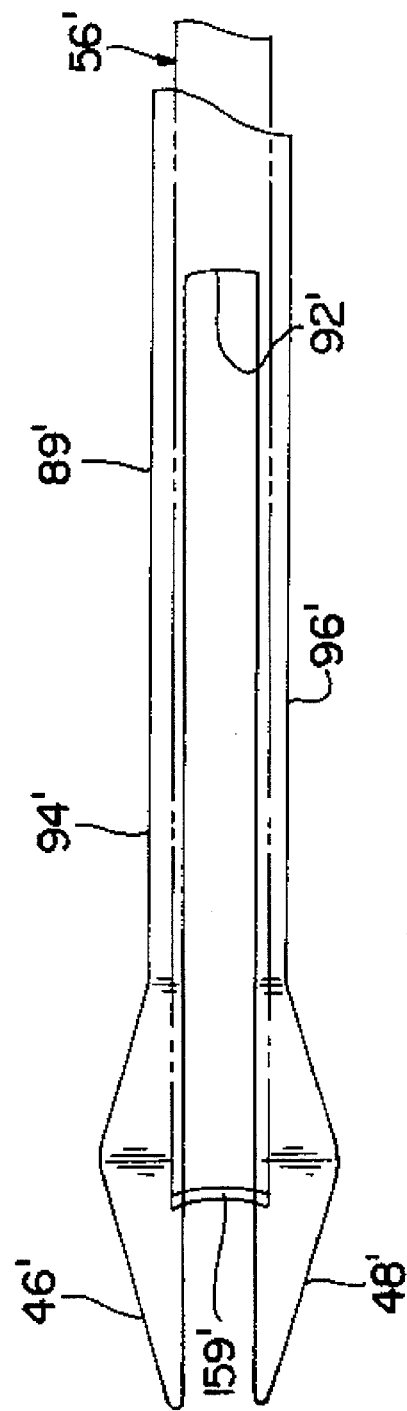
FIG. 8
FIG. 9

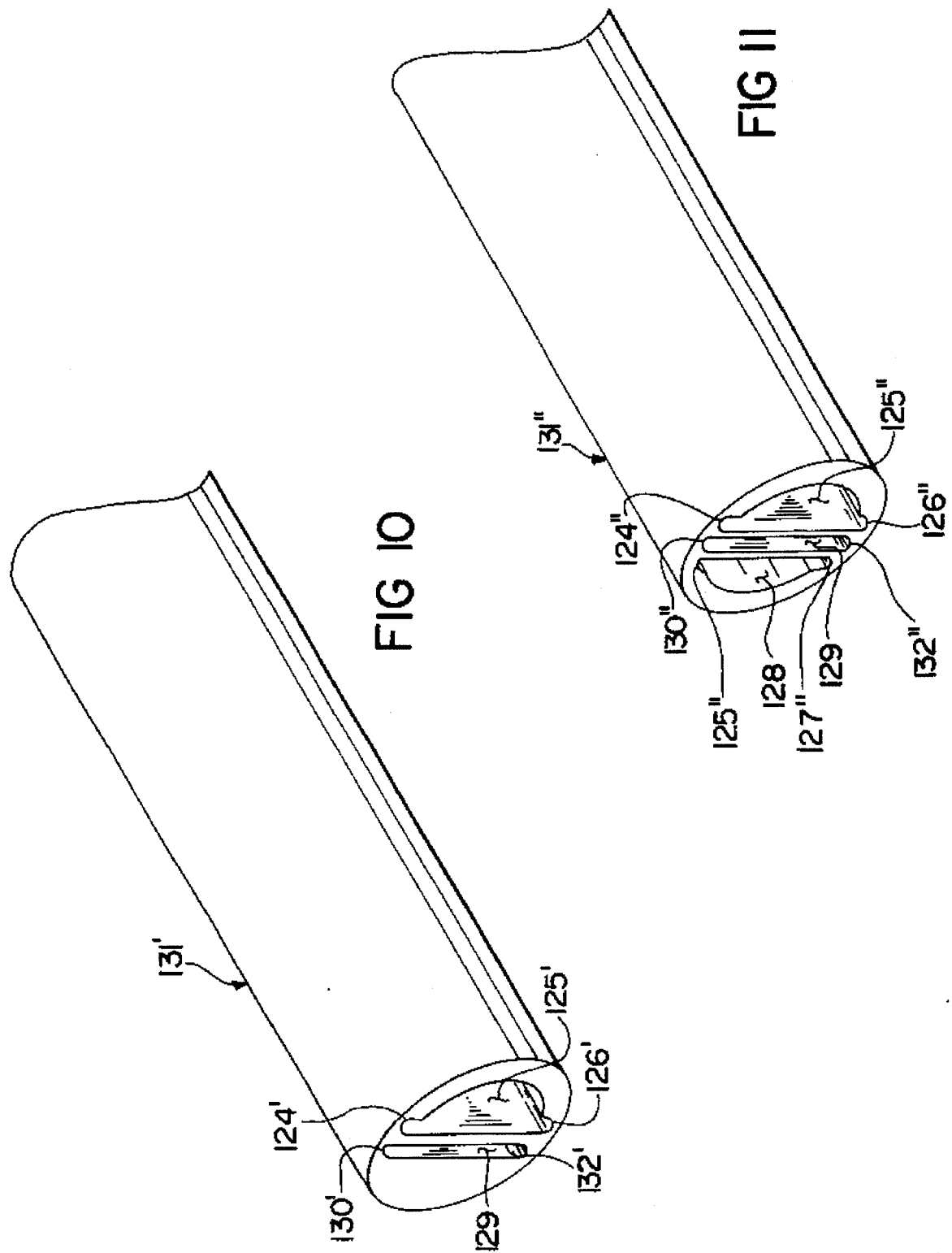

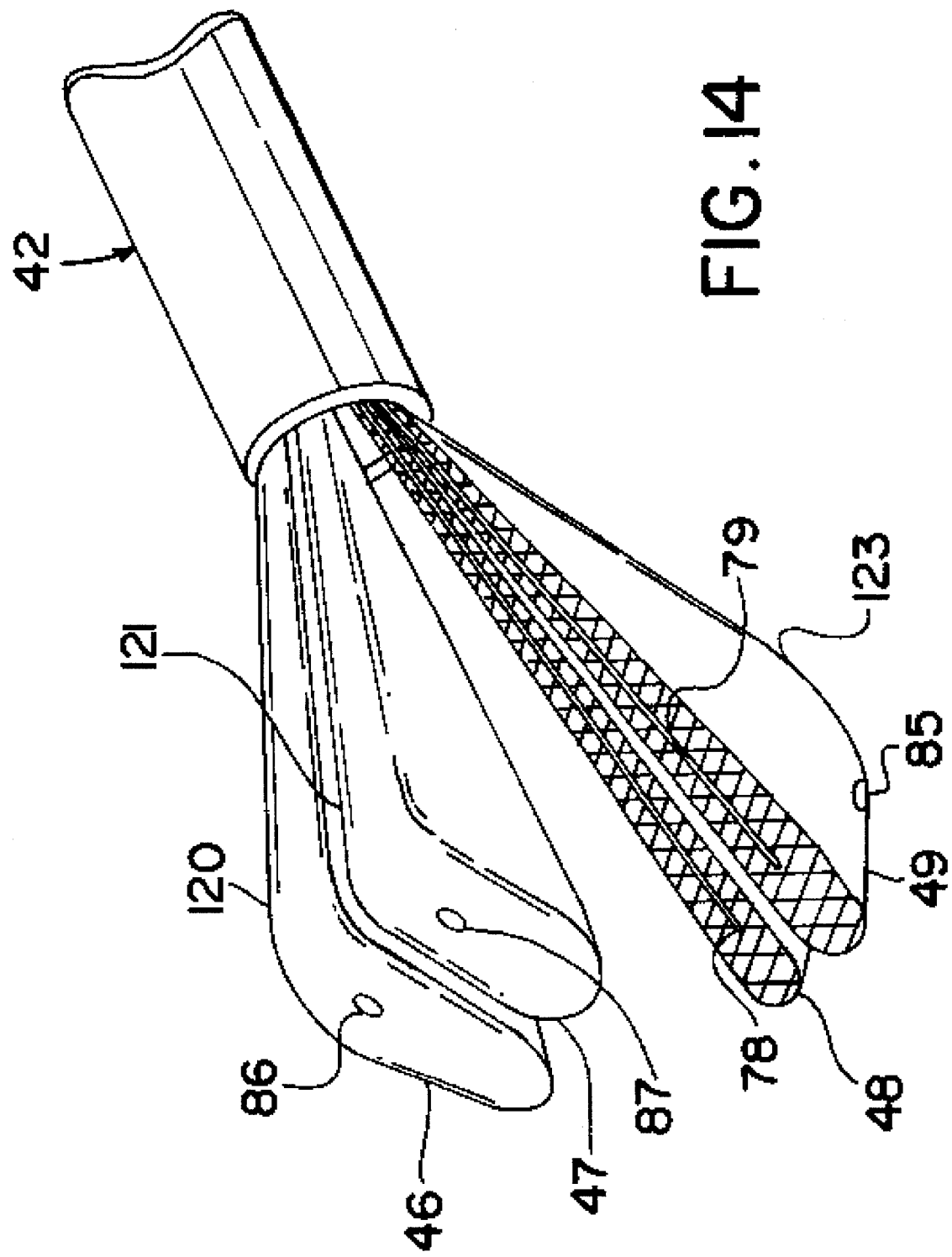

FIG.15

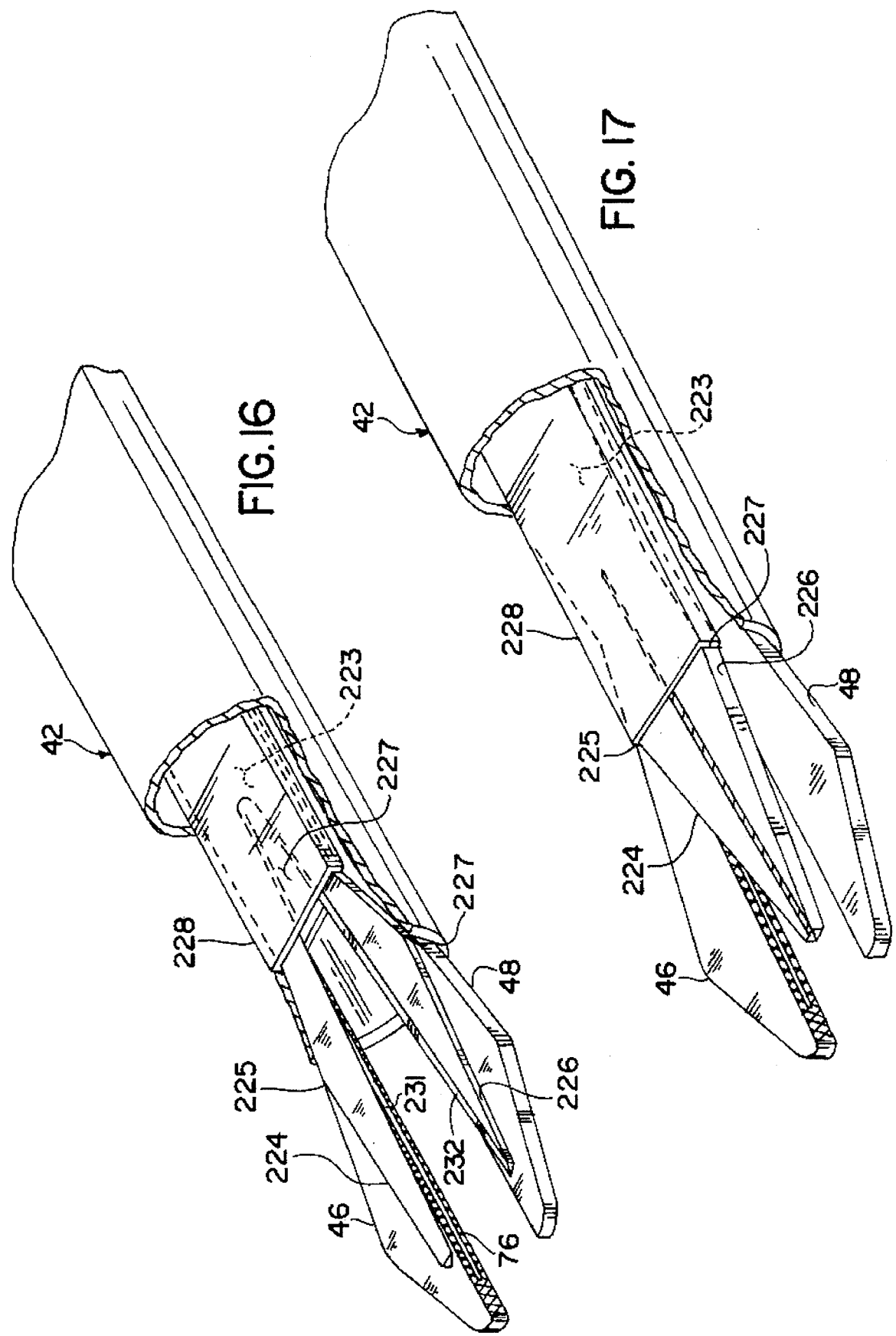

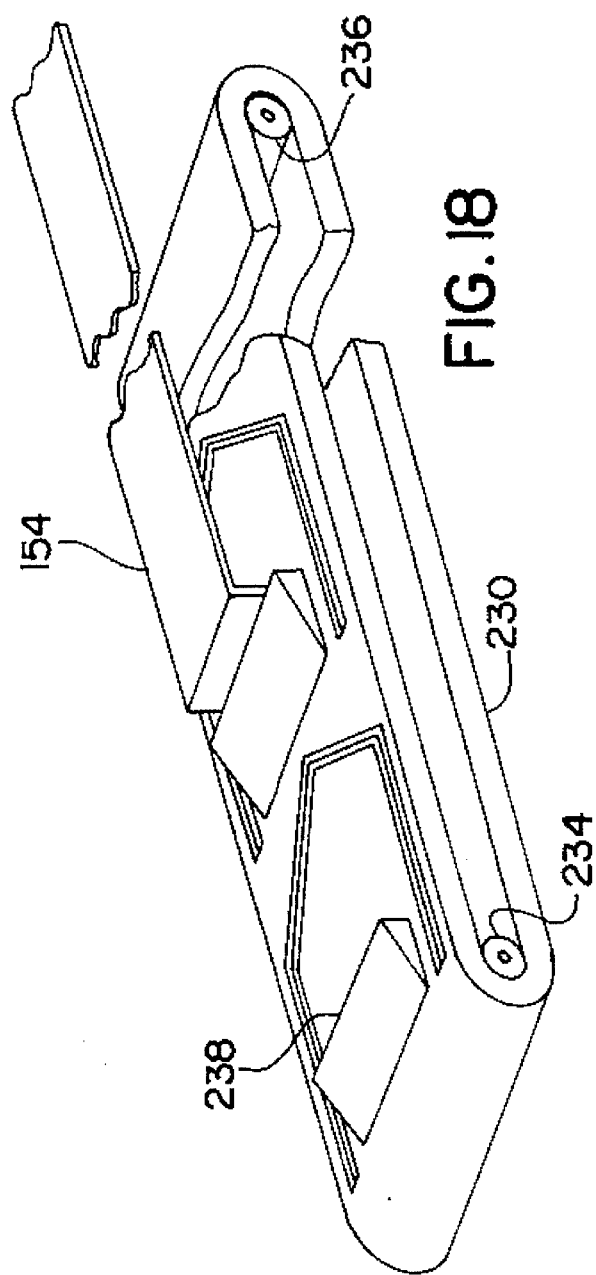
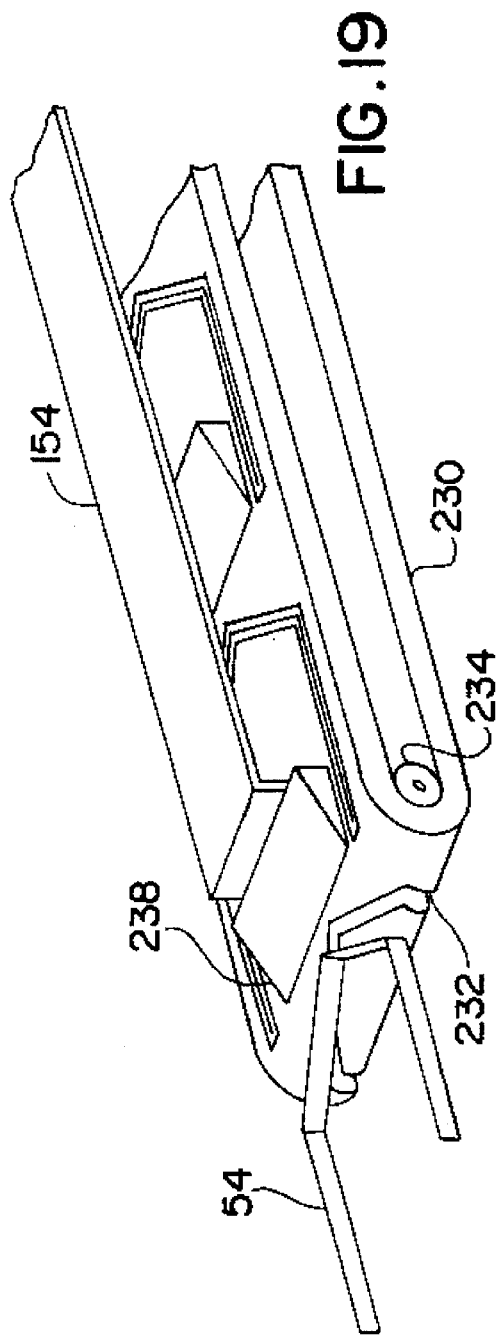

MULTIFUNCTIONAL CLIP APPLIER INSTRUMENT

CROSS-REFERENCE TO RELATED APPLICATIONS

This patent application is a continuation-in-part of patent application Ser. No. 08/045,769 filed Apr. 14, 1993, now abandoned which is a continuation-in-part of patent application Ser. No. 07/719,281 filed Sep. 18, 1991, now U.S. Pat. No. 5,366,459 which is a division of patent application Ser. No. 07/450,301 filed Dec. 15, 1989, now U.S. Pat. No. 5,100,418, which is a continuation-in-part of abandoned patent application Ser. No. 07/049,504 filed May 14, 1987, now abandoned. This patent application is also a continuation-in-part of patent application Ser. No. 951,275, filed Sep. 28, 1992, now U.S. Pat. No. 5,445,167, which is a division of above mentioned patent application Ser. No. 07/719,281 and which is a continuation-in-part of patent application Ser. No. 07/515,641 filed Apr. 2, 1990, now U.S. Pat. No. 5,171,250, which is a continuation of abandoned patent application Ser. No. 07/049,526 filed May 14, 1987, now abandoned. The disclosures of each of the above mentioned patent applications are incorporated herein by reference.

BACKGROUND OF THE INVENTION

1. Field of the Invention

The present invention relates generally to surgical instruments for applying surgical clips or staples to body tissue and, more particularly, to a multifunctional clip applier instrument for use in laparoscopic or endoscopic surgery having a plurality of selectively dispensable clips, forceps jaws for applying the clips to tissue or for manipulating and grasping tissue when no clip is in the forceps jaws and a selectively actuated cutting knife.

2. Discussion of the Prior Art

Endoscopic and, particularly, laparoscopic surgery has become well accepted since such surgery is less invasive than traditional open surgery and generally results in a reduced period of hospitalization and an accelerated recovery and convalescence. Because of the limited access, however, such surgery can be tedious and time-consuming. Surgical clips or staples, particularly useful in tissue ligation, are frequently used in endoscopic procedures. Early clip applier instruments held one clip in a pair of jaws inserted through a portal and placed around the tissue to be clipped. After each clip application, the instrument would have to be withdrawn and loaded with another clip, then reinserted. Subsequent clip applier instruments have been configured to automatically feed clips into the jaws from a magazine contained within the instrument body each time a clip is applied.

OBJECTS AND SUMMARY OF THE INVENTION

It is a primary object of the present invention to provide a multiple clip applier instrument for use in endoscopic surgery including forceps jaws useful for applying clips to tissue and that also can be used for grasping and manipulating tissue when no clip is placed in the jaws.

Another object of the present invention is to permit cutting with a multifunctional clip applier by forward movement of a cutter or knife blade along forceps jaws used to bend and clamp clips to tissue and/or to grasp and manipulate tissue.

A further object of the present invention is to selectively advance clips into the forceps jaws of a clip applier instrument.

The present invention has another object in that a multifunctional clip applier instrument includes suction and irrigation passages or tubes and cautery connections for use of the forceps jaws as monopolar or bipolar cautery electrodes.

Yet a further object of the present invention is to provide a multiple clip applier instrument that permits a scissor-like cutting function along forceps jaws and to bend and clamp clips to tissue and/or to grasp and manipulate tissue.

An additional object of this invention is to allow two spaced surgical clips to be applied simultaneously.

It is moreover an object of the current invention to provide a single device that can deliver and apply two clips of different type, size, shape or material to a remote surgical site.

A further additional object of this invention to allow two spaced surgical clips to be applied and a cutting procedure to be effected between the clips without removing or repositioning the device.

Some of the advantages of the present invention over the prior art are that cutting can be accomplished selectively or automatically following application of a clip to expedite the surgical procedure, loading or advancing of clips into the forceps jaws can be selective or automatic, suction and/or irrigation is available at the distal tips of the forceps jaws, and the instrument body and control housing can be reused with interchangeable clip cartridges or can be disposable after a single patient use.

The above and still further objects, features and advantages of the present invention will become apparent upon consideration of the following detailed description of a specific embodiment thereof, particularly when considered in conjunction with the accompanying drawings wherein like reference numerals in the various figures are utilized to designate like components.

BRIEF DESCRIPTION OF THE DRAWINGS

FIG. 3 is a broken perspective view of the forceps jaws of the multifunctional clip applier instrument of FIG. 1.

FIG. 4 is a section taken along line 4—4 of FIG. 3.

FIGS. 8 and 9 are side and top views, respectively, of a modification of the multifunctional clip applier instrument of the present invention.

FIG. 10 is a broken perspective view of a clip cartridge barrel with separate clip magazine and cutter blade channels.

FIG. 11 is a broken perspective view of a clip cartridge barrel with two clip magazine channels and a separate cutter blade channel.

FIG. 12 is a broken perspective view of forceps jaws having two clip grooves and a cutter groove.

FIG. 13 is a section taken along 13—13 of FIG. 12.

FIG. 14 is a broken perspective view of the distal end of the multifunctional clip applier instrument of the present invention having two pairs of forceps jaws.

FIG. 15 is a broken side view of the control housing of the present invention with two pusher plate rings.

FIGS. 16 and 17 show broken perspective views of the distal end of the multifunctional clip applier instrument of the present invention with scissor cutter blades in the open and closed positions respectively.

FIGS. 18 and 19 show an alternative clip advancement embodiment using a molded belt with a pusher plate.

DESCRIPTION OF THE PREFERRED EMBODIMENTS

Figure 1:
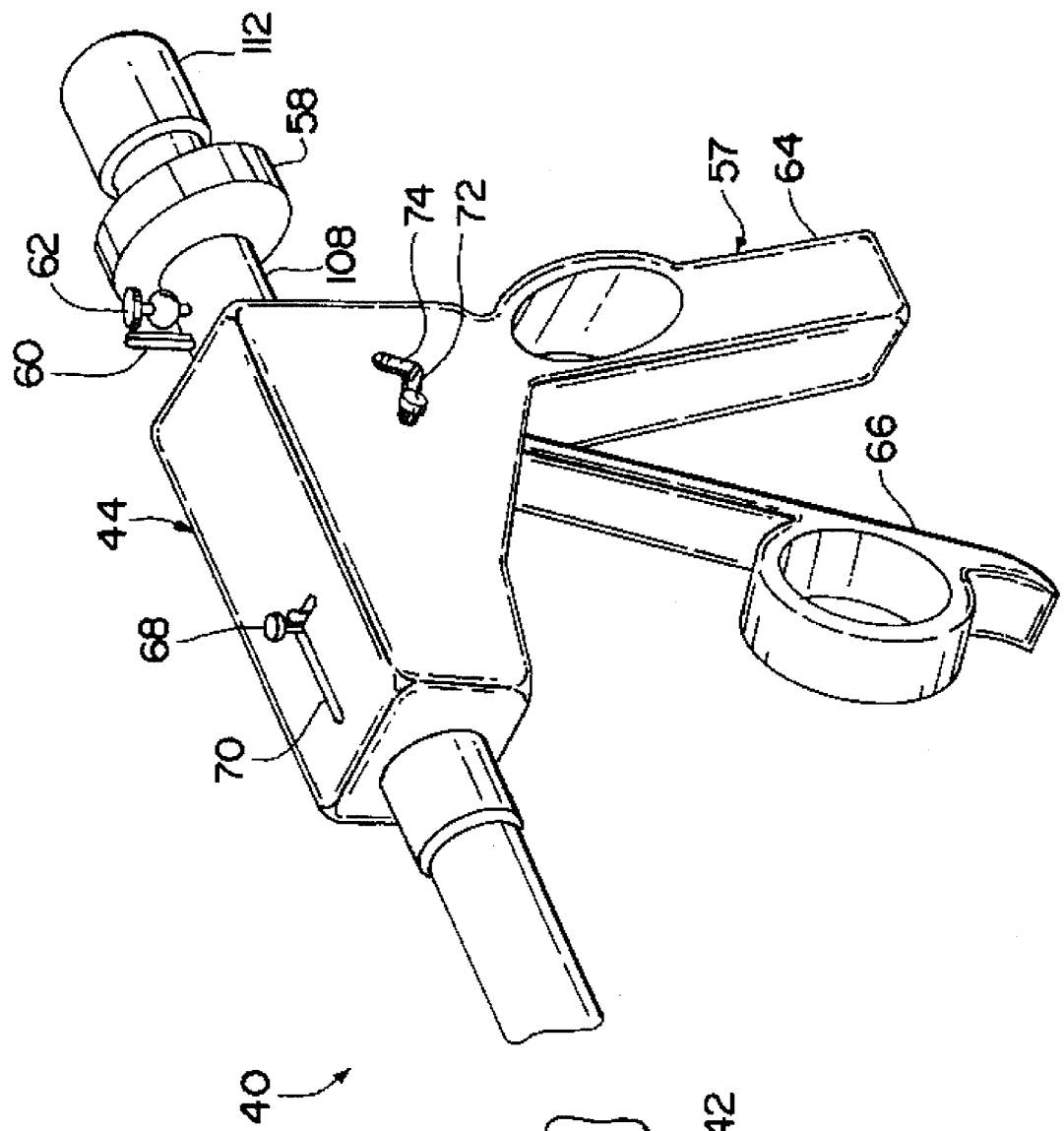
FIG. 1 is a broken perspective view of a multifunctional clip applier instrument according to the present invention.
Figure 2:
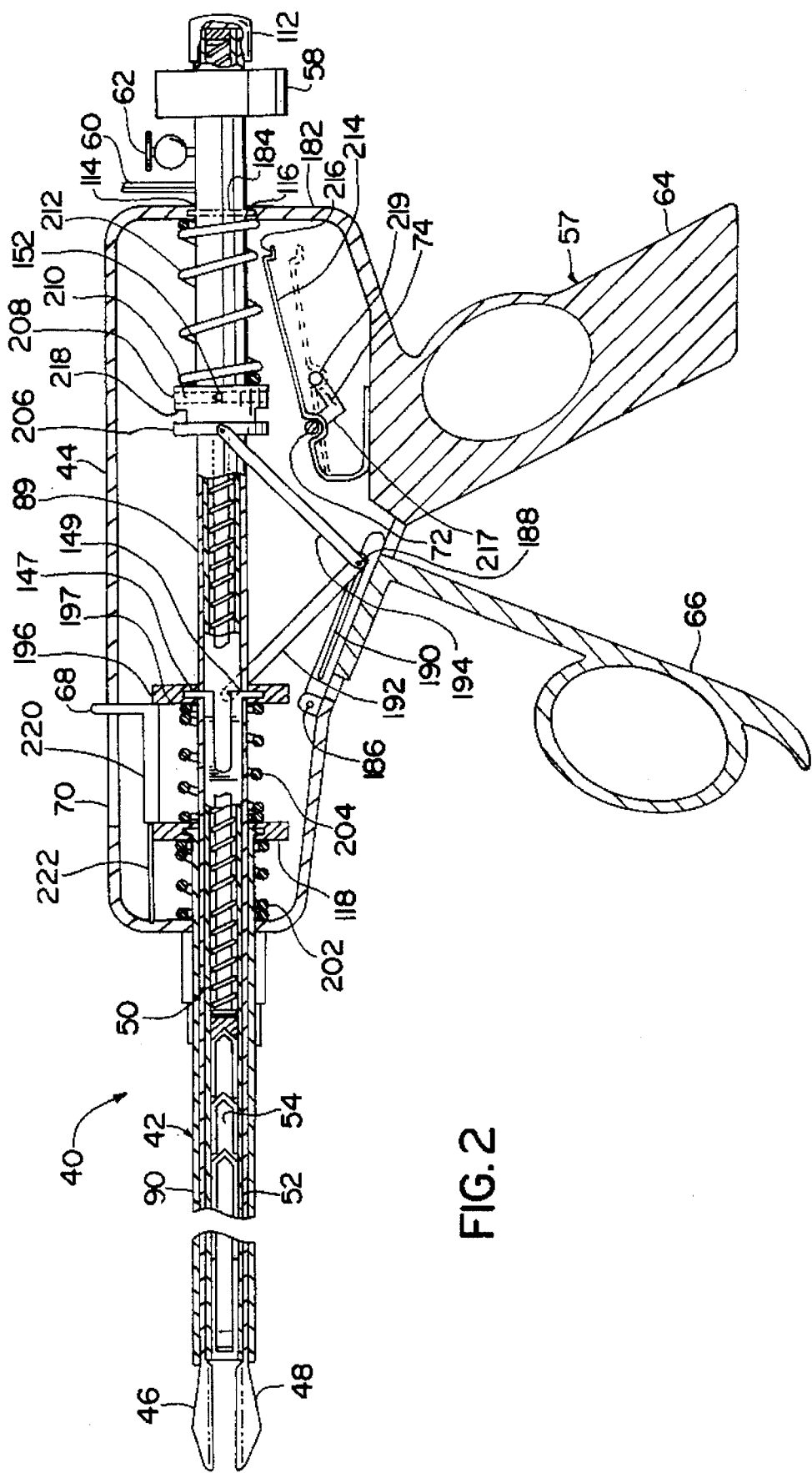
FIG. 2 is a broken side view of the multifunctional clip applier instrument of FIG. 1 with parts in section.

A multifunctional clip applier instrument or surgical stapler 40 for use in laparoscopic or endoscopic surgery according to the present invention is shown in FIGS. 1 and 2 and includes an elongate instrument body or shaft portion 42 having a proximal end coupled to and extending through a control housing or grip portion 44 and a pair of forceps jaws 46 and 48 or tip portion at a distal end thereof. A clip cartridge 50 is insertable into the instrument body and contains a clip magazine 52 housing a plurality of serially arranged surgical clips or staples 54 and a slidable cutter or knife blade 56 movable forwardly along the jaws to cut tissue held by the jaws.

Figure 5:
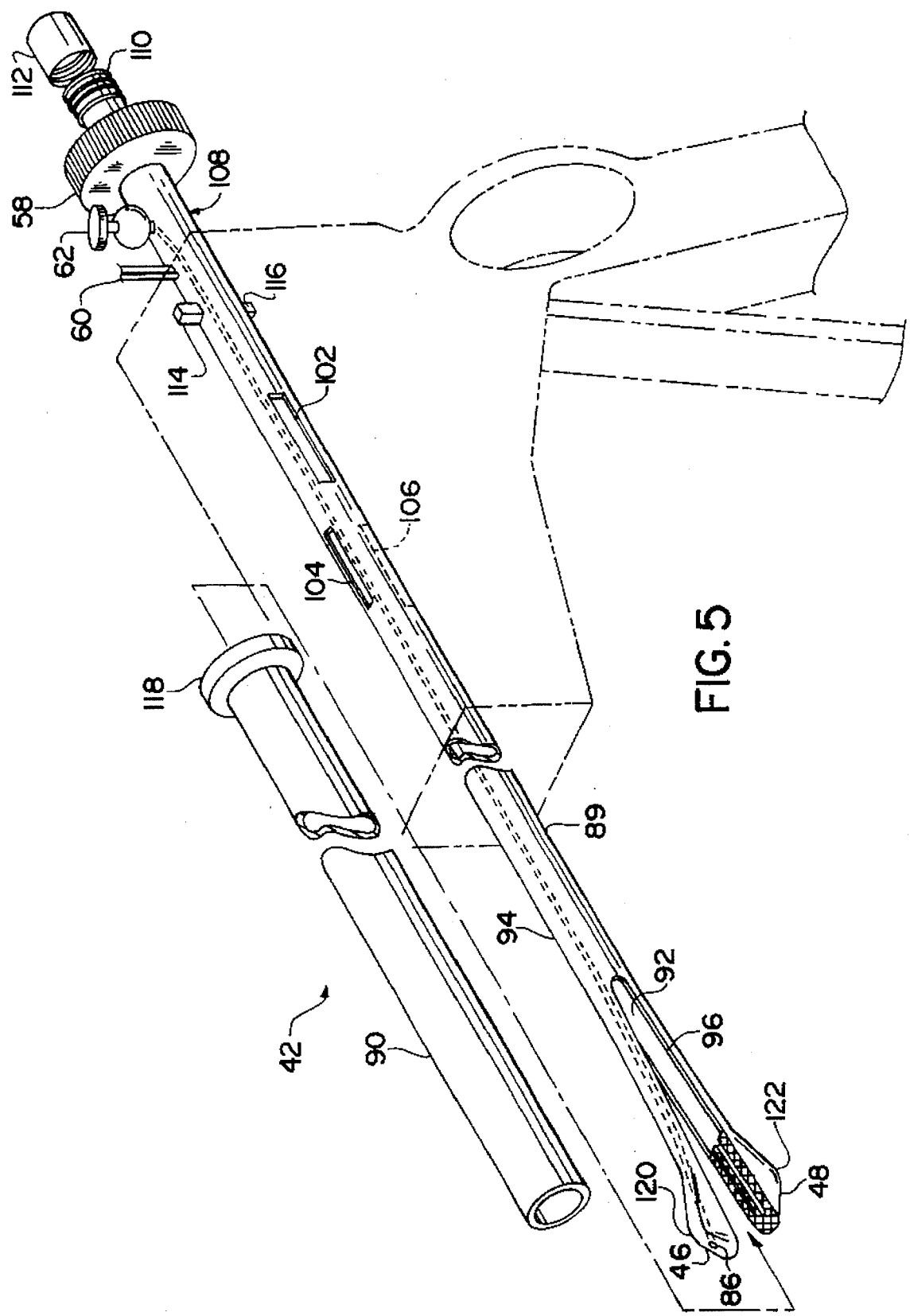
FIG. 5 is a broken, exploded perspective view of the instrument body of the multifunctional clip applier instrument of FIG. 1.

The elongate instrument body 42, as shown in FIG. 5, is formed of a hollow inner cylinder or member 89 extending through the control housing and a hollow outer cylinder or member 90 telescopically fitted around the inner cylinder 89. The inner cylinder has a slot or opening 92 along the distal portion defining spaced legs 94 and 96 carrying opposed forceps jaws 46 and 48. A slot 102 is cut along a proximal portion of the inner cylinder 89 to accommodate a spring tab extending from the clip cartridge within the instrument body to a pusher plate ring in the control housing as will be explained hereinafter. Opposed slots 104 and 106 are cut into the inner cylinder to accommodate fingers extending from cutter blade 56 as will be described later. A proximal portion 108 of the inner cylinder extends proximally beyond the control housing and carries an electric connector 60 extending transversely therefrom, a valve 62, and a rotation control knob 58, the inner cylinder terminating at a threaded open proximal end 110 which is closed by a threaded cap 112. The jaws 46 and 48 carry outer cams 120 and 122, respectively, and tubular passages 86 and 88 extend from the distal ends of jaws 46 and 48, respectively, to the proximal portion for communication with valve 62 to permit suction and/or irrigation at the distal end of the instrument. The inner cylinder is made of spring metal or other resilient material such that the legs 94 and 96 and the jaws 46 and 48 are spring biased away from each other. The forceps jaws 46 and 48, as shown in FIGS. 3 and 4, have grooves 76 and 78 extending longitudinally therealong, respectively, to guide and support the surgical clips and parallel longitudinal grooves 80 and 82 to guide and support the cutter blade. The interior opposed surfaces of the forceps jaws have knurled tissue-gripping configurations 84. The exterior surfaces can be coated in soft absorbent sponge-like material 83 to minimize manipulation damage to surrounding tissue, as illustrated in FIG. 4.

The outer cylinder 90 terminates proximally in an annular shoulder 118 within the control housing. Distal-proximal movement of the outer cylinder is initiated and controlled within the control housing by forces transmitted through a handle by the operating surgeon to shoulder 118. As the outer cylinder is urged distally, the distal end of the cylinder acts as a collar slidably engaging the forceps jaws to press the jaws toward each other overcoming the spring bias on legs 94 and 96.

Figure 6:
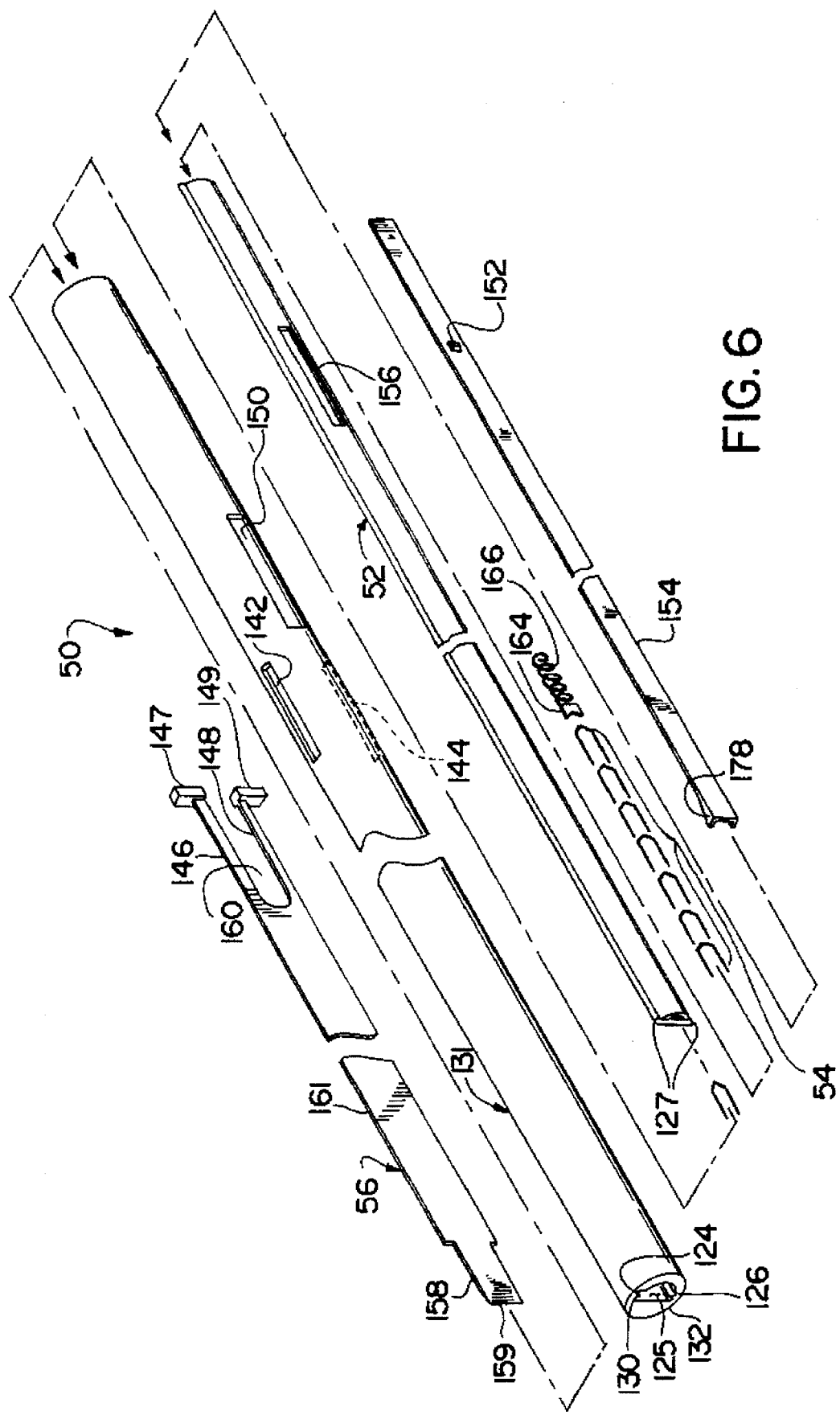
FIG. 6 is an exploded, perspective view of a cartridge for use with the multifunctional clip applier instrument of FIG. 1.

The clip cartridge 50, as shown in FIG. 6, includes a barrel 131 having a lumen 125 with a first pair of spaced, longitudinal, internal guide grooves 124 and 126 to receive longitudinal flanges 127 along opposite edges of the clip magazine 52 to align and support the clip magazine and a second pair of spaced, longitudinal internal guide grooves 130 and 132 to align and support the cutter blade. The barrel 131 has a distal pair of opposed slots 142 and 144 aligned with slots 104 and 106, respectively, in the inner cylinder when the cartridge is in place. Slots 104, 106, 142 and 144 permit passage of transversely extending fingers 147 and 149 carried on proximal arms 146 and 148, respectively, of the cutter blade 56 to be coupled with control housing mechanisms as will be described later. The barrel has a proximal slot 150 to permit passage of a spring tab 152 extending from a clip pusher plate 154 mounted in the clip magazine through an opening 156 in the clip magazine 52. The cutter blade has a narrowed distal end 158 terminating at a sharp edge 159 and sized to slide within the forceps jaws cutter grooves 80 and 82 when the jaws are in the closed position. The cutter grooves terminate distally at positions spaced proximally from the distal ends of the clip grooves 76 and 78 to prevent over-cutting of clipped tissue. The cutter blade has an elongate body or pusher portion extending along the length of body 42 from distal end 158 to a proximal portion having a slot 160 provided to allow resilient compression of the arms 146 and 148.

Figure 7:
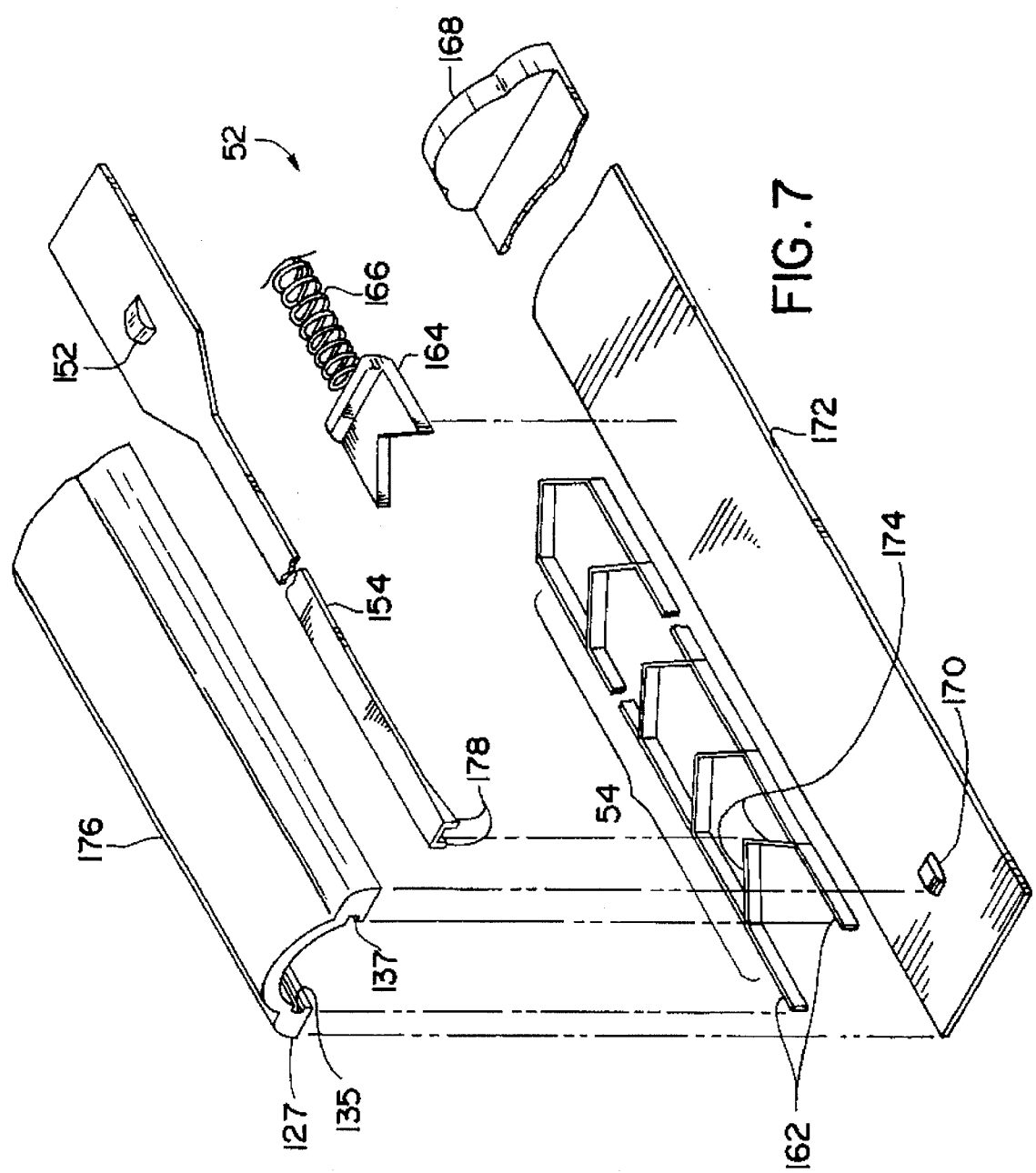
FIG. 7 is an exploded, perspective view of the clip magazine component of the cartridge of FIG. 6.

The clip magazine 52, as shown in FIG. 7, has a plurality of serially-arranged clips or staples 54, each clip having spaced legs 162 longitudinally aligned with the instrument body. The clips can be of conventional configuration, and the clip legs are guided within the clip magazine lumen by grooves 135 and 137. The clips are urged distally by a pusher 164 held compressively against the most proximal clip by a helical spring 166 mounted between the pusher and the clip magazine closed proximal end 168. The clips are prevented from moving distally by a spring tab 170 protruding from a flat side wall of the magazine 172 to restrain web sections 174 of the most distal clip. The pusher plate 154 is slidably mounted between a curved side wall 176 of the magazine and the clips 54. A distal portion of the pusher plate carries spaced, angled walls 178 forming a channel therebetween and extending downward to ride along side wall 172. The proximal portion of the pusher plate has a spring tab 152 that extends through slot 156 in the magazine 52, slot 150 in the barrel 131 and slot 102 in the inner cylinder 89. Tab 152 is coupled with control housing mechanism that will be described later, to slidably advance and retract the pusher plate to advance the most distal clip over the spring tab 170 and into the forceps jaws 46 and 48.

The instrument body inner cylinder 89 extends through the control housing 44, as shown in FIG. 2, and is held in place by pins 114 and 116 disposed in annular groove 184 in the proximal end wall 182 such that inner cylinder 89 is rotatable relative to the housing. The control housing 44 includes an operating handle 57 having a stationary grip member 64 and a pivotal grip member 66. A knife or cutter control lever 68 extends through a slot 70 in the top of the housing to permit the cutter blade to be optionally locked away from the tissue engaging forceps jaws. A clip advance control lever 72 extends through slot 74 on the control housing 44 to control the optional advancement of clips into the forceps jaws. The grip member 66 is pivotally connected to the housing by a pin 186. A slot 190 in the upper portion of the grip member 66 slidably receives a pin 188 pivotally connected to a lever arm 192 which is pivotally connected to a cutter ring 196 slidably encircling the inner cylinder and receiving the cutter blade fingers 147 and 149. A helical spring 202 encircles the proximal end of the outer cylinder and is mounted in compression between the control housing distal wall and the annular shoulder 118 of the outer cylinder. A helical spring 204 encircles the inner cylinder and is mounted in compression between the annular shoulder 118 and the cutter ring 196 to bias the cutter blade to a retracted position away from the forceps jaws. The spring constant or force of spring 204 is larger than the spring constant or force of spring 202 so that full distal displacement of the outer cylinder over the forceps jaws occurs before distal displacement of the cutter ring and cutter blade.

A lever arm 194 is pivotally attached to pin 188 and to a pusher ring 206 slidably encircling the inner cylinder. A pusher plate ring 208 slidably encircles the inner cylinder proximally of the pusher ring. The pusher plate ring 208 has an internal annular groove 210 to receive and engage spring tab 152 protruding from the proximal end of pusher plate 154. A helical spring 212 encircles the inner cylinder and is mounted in compression between the pusher plate ring and the housing body proximal wall. An upwardly biased leaf spring 214 is attached to a lower wall of the housing and extends proximally and upwardly toward the inner cylinder. The proximal end of the leaf spring has a notch 216 configured to engage an annular shoulder 218 on the pusher plate ring. The control lever 72 is mounted on a side wall of the housing and extends across the housing to project through slot 74 in the opposing housing wall. The slot 74 has a distal portion 217 and a proximal portion 219. When the lever is in the proximal slot portion 219, the lever holds the leaf spring away from the pusher plate ring; and, when the lever is in the distal slot portion 217, the leaf spring engages the shoulder of the pusher plate ring. Engagement and disengagement of the leaf spring with the pusher plate ring controls the pusher plate distal advance by the urging of the pusher plate ring and helical spring 212.

A spacer 220 is slidably mounted on a shaft 222 pivotally mounted to the distal wall of the housing. The spacer is configured to rigidly separate the annular shoulder 118 from the cutter ring 196. The cutter control lever 68, extending from the spacer upward through a slot 70 in the housing upper wall, allows the spacer to be pivotally displaced to an engaged position preventing relative displacement between the shoulder and ring or optionally pivoted out from between the shoulder 118 and the cutter ring 196. The slot 70 is L-shaped so that when the spacer is engaged, the cutter control lever 68 can move distally as the spacer is displaced along the shaft 222 by displacement of the annular shoulder and cutter ring.

In use, a clip cartridge 50 is loaded into the multifunctional clip applier instrument 40 through the open proximal end 110 of the instrument body 42, and the cap 112 is screwed into place. As the cartridge 50 is inserted into the inner cylinder 89, the spring tab 152 compresses and then locks into opening 210 in pusher plate ring 208 after passing through slot 102 in inner cylinder 89 while cutter blade fingers 147 and 149 compress and then lock into recesses 197 in cutter ring 196. Accordingly, the cartridge 50 is held in a precise operating position within the body 42 and the housing 44 and is mechanically coupled to the handle 57. The multifunctional clip applier instrument 40 is now ready for use in an endoscopic or laparoscopic procedure; and, prior to inserting the instrument through a portal sleeve to be received in an anatomical cavity, the control lever 68 is rotated to move spacer 220 to the engaged position between the cutter ring 196 and the outer cylinder shoulder 118 thereby preventing movement of the cutter blade. Once the instrument has been inserted through the portal sleeve, tissue can be grasped and manipulated by using the knurled surfaces 84 on the jaws 46 and 48 with the jaws being closed by squeezing grip members 64 and 66 causing grip member 66 to pivot counterclockwise looking at FIG. 2. Pivoting of grip member 66 causes lever 192 to move cutter ring 196 distally which, in turn, moves outer cylinder 90 distally via spacer 220 and shoulder 118 causing the distal end of the outer cylinder to act as a collar and engage cams 120 and 122 to close the jaws to engage tissue as desired. Due to the spacer 220 being disposed between the cutter ring 196 and the shoulder 118, the cutter blade 56 is prevented from moving distally to a position where the blade could enter the jaws. Accordingly, tissue cannot be inadvertently cut by the blade since the sharp distal end 159 of the cutter blade remains within the outer cylinder 90.

When the grip member 66 is pivoted toward the grip member 64, lever 194 moves pusher ring 206 and pusher plate ring 208 proximally to a position where shoulder 218 is engaged by notch 216 at the end of leaf spring 214 to lock the pusher plate ring in an inactive position. For this locked inactive condition to occur, lever arm 72 is moved to the distal slot portion 217 by the surgeon such that the leaf spring is in the position illustrated in FIG. 2. With the pusher plate ring 208 in the locked inactive position, no clip will be advanced into the jaws 46 and 48, and the jaws can be used to grasp tissue without engaging the tissue with a clip.

When it is desired to use the instrument to apply clips to tissue, the control lever 72 is moved into proximal slot portion 219 to a position shown in phantom in FIG. 2 wherein the leaf spring 214 is depressed to a position such that the notch 216 cannot engage the shoulder 218. When the pusher plate ring 208 is not engaged by the notch 216, spring 212 moves pusher plate ring 208 distally when the grip members are released such that the pusher plate 154 moves distally via the connection between pusher plate ring 208 and spring tab 152. This action causes the distal end 178 to engage the web portion 174 of the distal most clip 54 and push the clip distally over spring tab 170 and into the jaws 46 and 48 along grooves 76 and 78. The spring tab 170 will engage the next clip 54 to prevent movement of the next clip from the instrument body. The grip members are then squeezed again causing the jaws to close and bend the clip causing the legs 162 to clamp the tissue therebetween. Again, when the grip members are released, another clip will be loaded into the jaws unless control lever 72 has been returned to distal slot portion 217, it being appreciated that the clips 54 are urged distally under the bias of spring 166 and pusher 164. The angled walls of pusher plate distal end 178 allow the pusher plate to slide over the next clip when the grip members are squeezed to position the pusher plate to advance the next clip into the jaws.

When it is desired to cut tissue after a clip has been applied, spacer 220 is rotated out of the position between cutter ring 196 and shoulder 118 such that, upon squeezing of the grip members 64 and 66, a clip will initially be applied to tissue since spring 204 is stronger than spring 202; and, thereafter, cutter ring 196 will be moved distally relative to shoulder 118 causing the distal end of the cutter blade to slide into the jaws along grooves 80 and 82 to cut tissue clipped and held by the jaws. If it is desired to selectively cut tissue without immediately following clipping with a cutting action, no clip is loaded into the jaws and the spacer 220 is moved from the engaged position such that the cutter blade can be moved distally by squeezing the grip members 64 and 66.

If during a procedure it is desired to evacuate or aspirate fluid from the operative site, valve 62 can be coupled with a vacuum source to create suction through the inner cylinder 89 via passages or tubes 86 and 88 which open at the distal ends of the jaws 46 and 48, respectively. Similarly, irrigation at the operative site can be accomplished by supplying a fluid to valve 62 for injection at the operative site via the passages 86 and 88. If an additional valve is utilized at the proximal end of the inner cylinder, one passage 86 can be utilized for suction while the other passage 88 can be utilized for irrigation. Additionally, if bleeding occurs, the jaws 46 and/or 48 can be utilized as a cautery by applying electrical current to connector 60, it being noted that when the cautery connection is utilized, the inner cylinder will be made of an electrically conductive material and the surrounding component parts will be made of electrically insulating material.

After an operative procedure is completed, the entire instrument 40 can be disposed of or the cartridge 50 can be removed from the body 42 by removing cap 112 and applying a proximally directed force to the distal end of the cartridge causing the various interlocking components to compress allowing the cartridge to be ejected from the open end 110 of the inner cylinder. Once the cartridge is withdrawn, the remaining components of the multifunctional clip applier instrument, the elongate body and the control housing, can be sterilized and reused with a new sterile cartridge. By providing the knife or cutter blade along with the cartridge, it is assured that a sharp sterile blade is available for each procedure.

Where it is desired to provide a cutter blade with the instrument body rather than in the cartridge, the modification shown in FIGS. 8 and 9 can be utilized, the modification having reference numbers with primes corresponding to reference numbers utilized in instrument 40. In the modification of FIGS. 8 and 9, a cutter blade 56' extends along inner cylinder 89' externally of cartridge 50 and is connected to cutter ring 196 to move distally and proximally along with movement of the cutter ring in the same manner as described above. A cutter support and guide plate 250 is disposed along arms 94' and 96' to guide the blade 56' to follow the contour of the plate 250 and the forceps jaws 46' and 48'. As shown in FIG. 8, the forceps jaws 46' and 48' are angled relative to the longitudinal axis of the body 42. Accordingly, the cutter blade will move parallel to the forceps jaws 46' and 48' to cut tissue held by the jaws. The proximal end of the cutter blade 56' can be connected to a knob extending from housing 44 to allow movement of the cutter blade without squeezing the handle 57.

During a procedure, if it is desired to change the planar orientation of the forceps jaws, control knob 58 is grasped and rotated to rotate the inner cylinder 89 relative to the housing causing the plane of the forceps jaws to rotate to a desired position. The instrument 40 should be sealed, as is conventional, when the instrument is used in an insufflated anatomical cavity such as in laparoscopic procedures.

FIG. 6 shows a clip cartridge barrel 131 with a lumen 125 sized to house a single clip magazine 52 and a cutter blade 56 slidably adjacent to the clip magazine. FIGS. 10 and 11 show two alternate arrangements. In FIG. 10 the clip barrel 131' has a separate slot 129 to optionally receive a cutter blade that may or may not be disposable. Grooves 124' and 126' align clip magazine flanges in the lumen 125' and grooves 130' and 132' support and align the knife or cutter blade. FIG. 11 shows a clip cartridge barrel 131" similarly arranged with a separate cutter blade slot 129 but additionally carrying a second lumen 128 sized to receive a second clip magazine held in alignment by guide grooves 125" and 127". This dual clip magazine embodiment cooperates with forceps jaws 46 and 48 modified as shown in FIGS. 12 and 13, where a second pair of clip grooves 77 and 79 guide and support surgical clips from the second clip magazine into the tissue engaging space. Cutter guide grooves 80 and 82, are located between the first and second pair of clip guide grooves.

FIG. 14 shows two pairs of parallel forceps jaws, 46 and 48, and 47 and 49, each with clip guide grooves, 76 and 78, and 77 and 79, respectively. In this embodiment the cutter blade is aligned between the two pairs of forceps jaws or alternatively carried as a part of one pair in which case cutter guide grooves 80 and 82 would be incorporated into that pair of forceps jaws.

In use a multifunctional clip applier instrument embodied with the features of FIGS. 11–13 would be inserted through a portal sleeve into an anatomical cavity and used to grasp and manipulate tissue as described previously. Single clips could be applied as before using either of the clip magazines as the clip source. This increases the capacity of the instrument to carry a particular surgical clip, or optionally, permits the selective application of clips of different types, sizes, shapes or materials depending on the predetermined loading of the two clip magazines. The operating surgeon would advance a clip from the appropriate magazine into the tissue engaging space for application. Another procedure for which the features of the embodiment of FIGS. 11–13 is adapted is simultaneous parallel clip application, in which case the operating surgeon would advance clips into each pair of clip grooves before compressing the forceps jaws. By advancing the cutter blade into the tissue engaging space after applying a pair of clips but before repositioning the instrument, the surgeon can be assured of a precise cut between clips.

Figure 15:
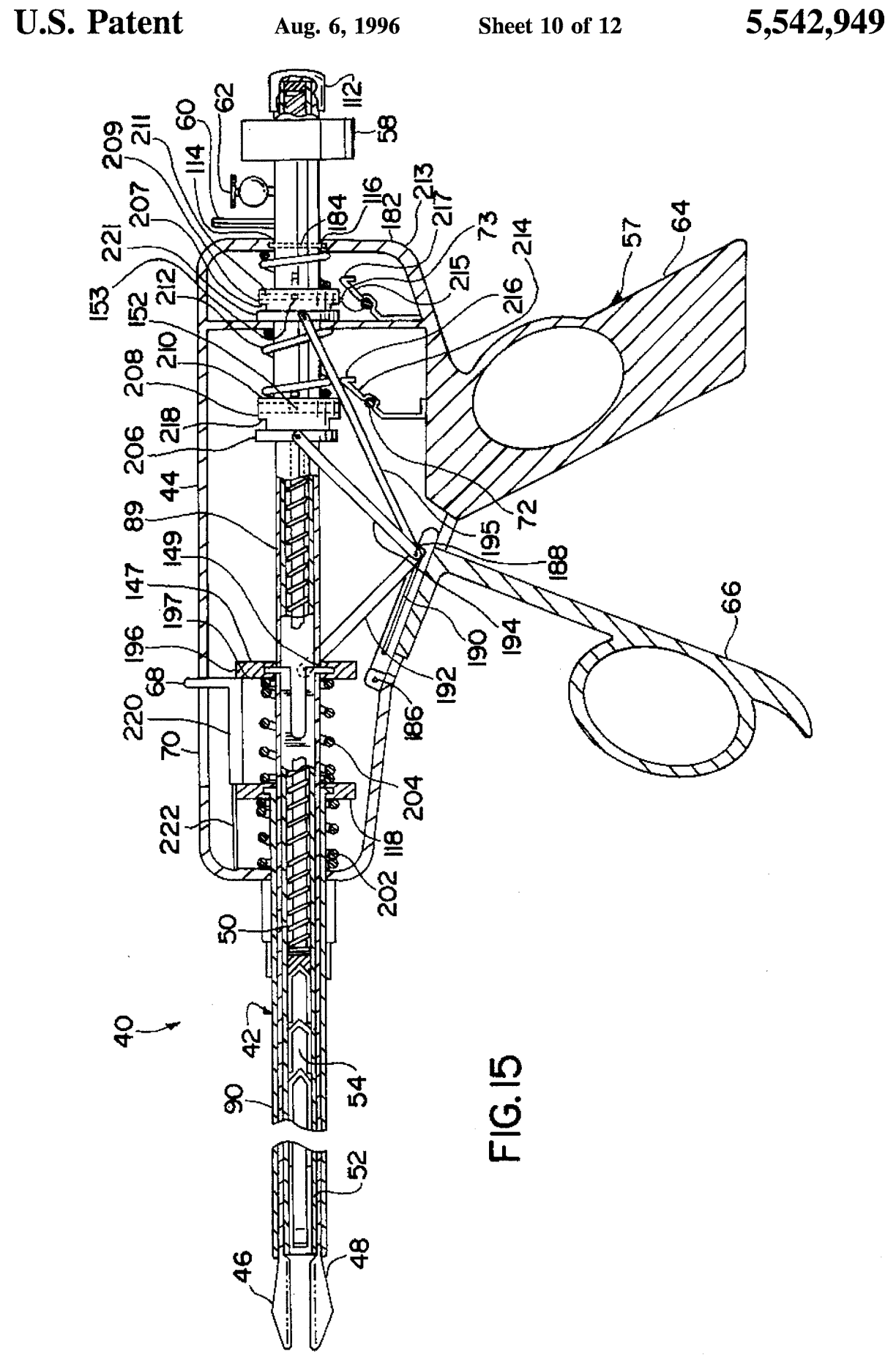

FIG. 15 shows the control housing for a multifunctional clip applier modified to selectively advance clips from two clip magazines. In this embodiment clips from the first clip magazine are advanced as described previously for FIG. 2. In addition a second lever arm 195 connected to pin 188 is attached to a second pusher ring 207 encircling inner cylinder 89. A second pusher plate ring 209 slidably encircles the inner cylinder and has an internal annular groove 211 which receives and engages a spring tab 153 protruding from a pusher plate in the second clip magazine. A helical spring 213 is mounted in compression between the pusher plate ring and the control housing body proximal wall. A second control lever 73 can be positioned to allow a notch 217 on a second leaf spring 215 to engage annular shoulder 221 on pusher plate ring 209. Engagement of the shoulder by the leaf spring prevents the pusher plate ring from advancing under the urging of the spring 213 and consequently prevents the advance of clips from the second magazine in the same fashion that the first leaf spring can be positioned to allow or prevent clips from being advanced from the first clip magazine. Consequently if neither leaf spring is positioned to engage a pusher plate ring shoulder, clips from both magazines will be advanced into the jaws for simultaneous clip application. Engagement of both leaf springs with pusher plate ring shoulders will permit no clip to advance and the forceps jaws can be used for tissue manipulation. Alternately clips of either magazine can be positioned for tissue application.

FIGS. 16 and 17 show the distal end of the present invention having a cutting member 223 with a slot 221 to define two spaced scissor-like cutting blades 224 and 226 carrying sharpened opposed inner surfaces 231 and 232. Cutter member 223 is made of spring metal or other resilient material such that cutter blades 224 and 226 are spring biased away from each other. Cutter member 223 is housed in a slidable casing 228 which can be urged distally from the control housing. As casing 228 moves distally relative to cutter member 223, as shown in FIG. 17, cams 225 and 227 on cutter blades 224 and 226 are engaged and urged toward each other to cut tissue held therebetween. The cutter 223 and housing 228 constitute a cutter cartridge which can be slidably mounted to allow retraction or extension of the cutter and housing into the instrument body during periods when no cutting is contemplated or distally beyond the forceps jaws.

Slot 221 can be shaped to produce cutting uniformly and evenly between parallel cutter blades or biased to produce a cut beginning distally and moving in the proximal direction or vice versa. FIGS. 16 and 17 show cutter blades shaped to cut from the proximal toward distal directions. Although FIGS. 16 and 17 show the cutting blades located adjacent to the forceps jaws 46 and 48, they could as well be positioned between parallel pairs of forceps jaws or located within grooves in the forceps jaws opposed inner surfaces.

FIGS. 18 and 19 show an alternative clip transport mechanism for use in the multifunctional clip applier. A flexible molded belt 230 travels freely around rollers 234 and 236. Indentations 232 are molded into the belt to hold and carry surgical clips 54 and wedge-shaped protrusions 238 extend from the belt and are engaged by the pusher plate 154. As the pusher plate is advanced against the wedge-shaped protrusion the belt curves sharply around roller 234 and the clip 54 is advanced and released from the belt. As the pusher plate retracts it slides up and over the next wedge-shaped protrusion into position to repeat the sequence.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces.

2. A multifunctional clip applier instrument as recited in claim 1 further comprising a locking member coupled with said pusher member to selectively prevent advancement of said clips.

3. A multifunctional clip applier instrument as recited in claim 1 further comprising a cutter blade carried by said elongate body and adapted to move along said forceps jaws into and out of said tissue-engaging space to sever tissue held therebetween, and means located on said proximal end of said elongate body to selectively control movement of said cutter blade.

4. A multifunctional clip applier instrument as recited in claim 3 further comprising a cutter control member coupled with said cutter blade to selectively prevent movement of said cutter blade.

5. A multifunctional clip applier instrument as recited in claim 3 wherein said cutter blade slides adjacent said forceps jaws to cut tissue held in said tissue-engaging space.

6. A multifunctional clip applier instrument as recited in claim 1 wherein said forceps jaws have clip grooves extending along said opposed inner surfaces sized to receivingly engage and guide said surgical clip legs into said tissue-engaging space.

7. A multifunctional clip applier instrument as recited in claim 6 further comprising a clip cartridge sized to insertably fit into said elongate body, said clip cartridge supporting a clip magazine housing said plurality of surgical clips in serial alignment parallel to said body longitudinal axis, said clip magazine having means to align said clip legs with said clip grooves on said opposed inner surfaces.

8. A multifunctional clip applier instrument as recited in claim 7 wherein said clip cartridge sized to insertably fit into said elongate body can be adapted to support said clips of various types sizes, shapes and materials such that said clip applier instrument can be used to interchangeably apply a variety of said surgical clips.

9. A multifunctional clip applier instrument as recited in claim 1 wherein said opposed inner surfaces have knurled tissue-engaging finishes.

10. A multifunctional clip applier instrument as recited in claim 1 wherein said forceps jaws are provided with a coating of soft sponge-like material on all exterior surfaces except said opposed inner surfaces.

11. A multifunctional clip applier instrument as recited in claim 1 wherein said elongate body has a longitudinal axis and said forceps jaws are disposed at an angle to said body longitudinal axis.

12. A multifunctional clip applier instrument as recited in claim 1 further comprising means for connecting said proximal end to a vacuum producing means and means for communicating said vacuum to said distal end.

13. A multifunctional clip applier instrument as recited in claim 1 further comprising means for connecting said proximal end to irrigation means and means for communicating said irrigation to said distal end.

14. A multifunctional clip applier instrument as recited in claim 1 further comprising means for attaching said proximal end to cautery producing means and means for communicating said cautery to said distal end.

15. A multifunctional clip applier instrument as recited in claim 1 further comprising means to rotate said elongate body relative to said proximal end.

16. A multifunctional clip applier instrument as recited in claim 1 further comprising a pair of opposed cutter blades carried by said elongate body and extending along said forceps jaws and means carried by said elongate body to selectively compress said opposed cutter blades in a scissor-like manner to bring said cutter blades into overlapping contact one with the other effecting severing of tissue therebetween.

17. A multifunctional clip applier instrument as recited in claim 16 wherein said opposed cutter blades are selectively retractable proximally from said forceps jaws.

18. A multifunctional clip applier instrument as recited in claim 16 wherein said opposed cutter blades are selectively extendable distally beyond said forceps jaws.

19. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces, a cutter blade carried by said elongate body and adapted to move along said forceps jaws into and out of said tissue-engaging space to sever tissue held therebetween, and means located on said proximal end of said elongate body to selectively control movement of said cutter blade, wherein said forceps jaws have cutter grooves extending along said opposed inner surfaces sized to receivingly engage and guide said cutter blade.

20. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, wherein said forceps jaws have clip grooves extending along said opposed inner surfaces sized to engage and guide said surgical clip legs into said tissue-engaging space, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces, a clip cartridge sized to insertably fit into said elongate body, said clip cartridge supporting a clip magazine housing said plurality of surgical clips in serial alignment parallel to said body longitudinal axis, said clip magazine having means to align said clip legs with said clip grooves on said forceps jaws opposed inner surfaces, wherein said clip cartridge is removable from said elongate body and disposable.

21. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, wherein said forceps jaws have clip grooves extending along said opposed inner surfaces sized to engage and guide said surgical clip legs into said tissue-engaging space, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces, a clip cartridge sized to insertably fit into said elongate body, said clip cartridge supporting a clip magazine housing said plurality of surgical clips in serial alignment parallel to said body longitudinal axis, said clip magazine having means to align said clip legs with said clip grooves on said forceps jaws opposed inner surfaces, wherein said clip cartridge is removable from said elongate body and is reloadable with additional surgical clips.

22. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, wherein said forceps jaws have clip grooves extending along said opposed inner surfaces sized to engage and guide said surgical clip legs into said tissue-engaging space, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces, a clip cartridge sized to insertably fit into said elongate body, said clip cartridge supporting a clip magazine housing said plurality of surgical clips in serial alignment parallel to said body longitudinal axis, said clip magazine having means to align said clip legs with said clip grooves on said forceps jaws opposed inner surfaces, wherein said clip cartridge further comprises a cutter blade, adapted to move along said forceps jaws into and out of said tissue-engaging space to sever tissue held therebetween, and said instrument has means located on said proximal end of said elongate body to selectively control movement of said cutter blade.

23. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a pair of forceps jaws having opposed inner surfaces defining a tissue-engaging space therebetween, a plurality of surgical clips disposed within said elongate body, said clips each having opposed legs movable from an open spaced condition to a closed condition adjacent each other to engage tissue therebetween, said jaws having a clip receiving position defining a space between said opposed inner surfaces corresponding to the size and shape of said clip legs in said open spaced condition, an advancing mechanism carried by said elongate body and including a pusher member movable distally to advance a distalmost surgical clip into said space between said opposed inner surfaces, said elongate body comprising means for selectively compressing said forceps jaws toward one another both prior to and subsequent to advancement of a clip into said space between said opposed inner surfaces, first and second clip magazines sized to insertably fit simultaneously into a clip cartridge, said clip cartridge being sized to insertably fit into said elongate body, said first and second clip magazines each supporting said plurality of surgical clips in serial alignment parallel to said body elongate axis, said forceps jaws having a pair of displaced parallel clip grooves extending along said opposed inner surfaces sized to receivingly engage and guide said surgical clip legs into said tissue-engaging space, said first and second clip magazines having means to align said clip legs with said parallel clip grooves.

24. A multifunctional clip applier instrument as recited in claim 23 further comprising means carried by said elongate body for selectively advancing clips into said space between said opposed inner surfaces from said first clip magazine and said second clip magazine simultaneously.

25. A multifunctional clip applier instrument as recited in claim 23 further comprising means carried by said elongate body for selectively advancing clips into said space between said opposed inner surfaces from said first clip magazine, and independent means for selectively advancing clips into said space between said opposed inner surfaces from said second clip magazine.

26. A multifunctional clip applier instrument as recited in claim 23 further comprising a cutter blade carried by said elongate body and adapted to move along said forceps jaws into and out of said tissue-engaging space to sever tissue held therebetween.

27. A multifunctional clip applier instrument as recited in claim 26 wherein said forceps jaws have cutter grooves extending along said opposed inner surfaces and between said pair of displaced parallel clip grooves and sized to receivingly engage and guide said cutter blade.

28. A multifunctional clip applier instrument as recited in claim 26 wherein said cutter blade slides adjacent to said forceps jaws to cut tissue held in said tissue-engaging space.

29. A multifunctional clip applier instrument for use in endoscopic surgical procedures performed in an anatomical cavity comprising:

an elongate body having a proximal end for positioning at a location external to the anatomical cavity and a distal end for positioning within the anatomical cavity, said distal end comprising a first and a second pair of forceps jaws, each of said forceps jaws pairs having opposed inner surfaces defining tissue-engaging spaces therebetween, a plurality of surgical clips disposed within said elongate body, said clips each having opposed legs movable from an open spaced condition to a closed condition adjacent each other to engage tissue therebetween, said forceps jaws pairs each having a clip receiving position defining a space between said opposed inner surfaces corresponding to the size and shape of said clip legs in said open condition, said elongate body comprising means for selectively compressing said forceps jaws pairs toward one another, said proximal end of said elongate body comprising means for controlling advancement of said clips and means for controlling compression of said forceps jaws pairs.

30. A multifunctional clip applier instrument as recited in claim 29 further comprising first and second clip magazines sized to insertably fit simultaneously into a clip cartridge, said clip cartridge being sized to insertably fit into said elongate body, said first and second clip magazines each supporting said plurality of surgical clips in serial alignment parallel to said body elongate axis, said forceps jaws pairs each having clip grooves extending along said opposed inner surfaces sized to engage and guide said surgical clip legs into said tissue engaging spaces, said first clip magazine having means to align said clip legs with said clip grooves on said first pair of forceps jaws and said second clip magazine having means to align said clip legs with clip grooves on said second pair of forceps jaws.

31. A multifunctional clip applier instrument as recited in claim 30 further comprising means carried by said elongate body for selectively advancing clips from said first clip magazine into said space between said opposed inner surfaces of said first pair of forceps jaws and from said second clip magazine into said space between said opposed inner surfaces of said second pair of forceps jaws simultaneously.

32. A multifunctional clip applier instrument as recited in claim 30 further comprising means for selectively advancing clips from said first clip magazine into said space between said opposed inner surfaces of said first pair of forceps jaws, and independent means for selectively advancing clips from said second clip magazine into said space between said opposed inner surfaces of said second pair of forceps jaws.

33. A multifunctional clip applier instrument as recited in claim 30 further comprising a cutter blade carried by said elongate body and movable along said forceps jaws pairs to cut tissue held in said tissue engaging spaces.

34. A multifunctional clip applier instrument as recited in claim 33 wherein said cutter blade slides between said first pair of forceps jaws and said second pair of forceps jaws.

35. A multifunctional clip applier instrument as recited in claim 33 wherein said first pair of forceps jaws have cutter grooves extending along said opposed inner surfaces of said first pair of forceps jaws sized to receivingly engage and guide said cutter blade.

* * * * *